(12) United States Patent
Nakamura

(10) Patent No.: US 9,101,528 B2
(45) Date of Patent: Aug. 11, 2015

(54) GAS MIST PRESSURE BATHING METHOD AND GAS MIST PRESSURE BATHING SYSTEM

(71) Applicant: Shoichi Nakamura, Nagano (JP)

(72) Inventor: Shoichi Nakamura, Nagano (JP)

(73) Assignees: ACP JAPAN CO., LTD., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 163 days.

(21) Appl. No.: 14/113,732

(22) PCT Filed: Nov. 1, 2012

(86) PCT No.: PCT/JP2012/078312
§ 371 (c)(1),
(2) Date: Oct. 24, 2013

(87) PCT Pub. No.: WO2013/065778
PCT Pub. Date: May 10, 2013

(65) Prior Publication Data
US 2014/0046247 A1 Feb. 13, 2014

(30) Foreign Application Priority Data
Nov. 4, 2011 (JP) ................................. 2011-242316

(51) Int. Cl.
*A61M 37/00* (2006.01)
*A61H 33/02* (2006.01)
(Continued)

(52) U.S. Cl.
CPC ................ *A61H 33/02* (2013.01); *A61H 33/14* (2013.01); *A61K 33/00* (2013.01);
(Continued)

(58) Field of Classification Search
CPC .................. A61H 2033/143; A61H 2033/145; A61H 2201/0157; A61H 2201/164; A61H 2201/165; A61H 2205/06; A61H 2205/065; A61H 2205/067; A61H 2205/106; A61H 2205/12; A61H 33/02; A61H 33/14
USPC ........................................ 604/23, 24; 607/84
See application file for complete search history.

(56) References Cited

U.S. PATENT DOCUMENTS

2010/0305497 A1   12/2010   Tanaka et al.
2011/0208116 A1   8/2011    Nakamura

FOREIGN PATENT DOCUMENTS

JP   2009-183625 A   8/2009

*Primary Examiner* — Kevin C Sirmons
*Assistant Examiner* — Deanna K Hall
(74) *Attorney, Agent, or Firm* — Manabu Kanesaka

(57) ABSTRACT

Provided are a gas mist pressure bathing method and a gas mist pressure bathing system that improve the efficiency of absorbing a gas mist from the skin and mucous membranes of a living body. The gas mist pressure bathing method is provided with a first step, a second step and a third step. The first step involves supplying a gas mist and gas for a predetermined time to at least a first cover 51 of a living body cover member 50 having said first cover 51 and a second cover 55 positioned outside of the first cover 51, the inside of said second cover 55 being substantially sealed; covering the skin and mucous membranes of the living body; and forming a space wherein the gas mist and gas supplied by a gas mist generating means 30 are sealed. The second step involves discharging the gas mist and gas from the first cover 51 and/or the second cover 55. The third step involves supplying the gas mist and gas for a predetermined time from the gas mist generating means 30 to the first cover 51 and the second cover 55, and keeping the pressure inside at least the second cover 55 in a predetermined range. The first to third steps are repeated multiple times.

23 Claims, 14 Drawing Sheets

Figure 1:
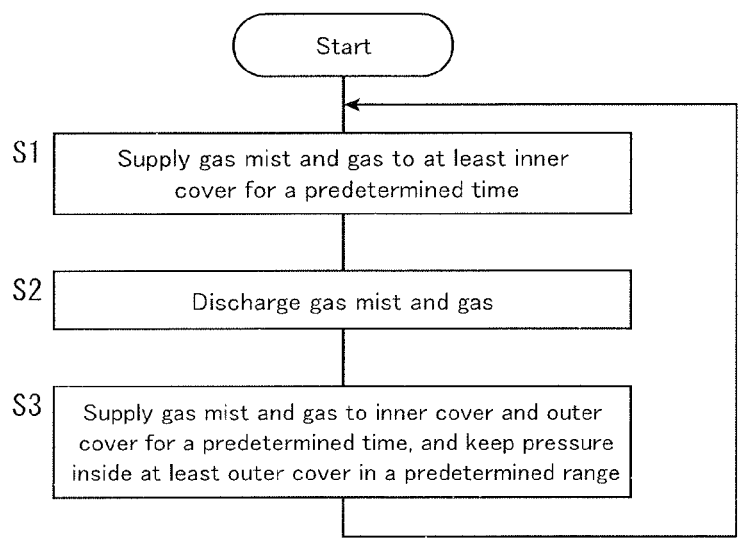

(51) Int. Cl.
 *A61H 33/14* (2006.01)
 *A61K 33/00* (2006.01)
(52) U.S. Cl.
 CPC .... *A61H 2033/143* (2013.01); *A61H 2033/145* (2013.01); *A61H 2201/0157* (2013.01); *A61H 2201/0207* (2013.01); *A61H 2201/164* (2013.01); *A61H 2201/165* (2013.01); *A61H 2201/5082* (2013.01); *A61H 2205/06* (2013.01); *A61H 2205/065* (2013.01); *A61H 2205/067* (2013.01); *A61H 2205/106* (2013.01); *A61H 2205/12* (2013.01)

GAS MIST PRESSURE BATHING METHOD AND GAS MIST PRESSURE BATHING SYSTEM

RELATED APPLICATIONS

The present application is National Phase of International Application No. PCT/JP2012/078312 filed Nov. 1, 2012, and claims priority from Japanese Application No. 2011-242316, filed Nov. 4, 2011.

TECHNICAL FIELD

The present invention relates to a gas mist pressure bathing method and a gas mist pressure bathing system for improving absorption efficiency of gas into a skin or a mucous membrane of a living body, in which a gas mist is prepared by pulverizing liquid into micron sized mists and dissolving oxygen or carbon dioxide, or a mixed gas of oxygen, carbon dioxide, and the gas mists are caused to directly contact the skin and mucous membrane of the living body at pressure of not less than a predetermined value.

BACKGROUND OF THE INVENTION

Conventionally, it has been known that carbon dioxide (carbonic acid anhydride: $CO_2$) has two properties of being not only soluble in water (water-soluble) but also soluble in fat (fat-soluble) and, owing to such both properties, when only contacting to the skin and the mucous membrane of the living body, which are like as mixed with water and fat, carbon dioxide penetrates and expands blood vessels around the penetrated parts, and it works to improve a blood circulation. By this action of accelerating the blood circulation, it displays various physiological effects such as dropping of blood pressure, improving of metabolism or accelerating to remove pain substances or waste products. Further, it has also anti-inflammation and anti-bacterial function.

Further, recently, oxygen of high concentration has also widely been known as being effective over activity of metabolism or acceleration of blood circulation. Other than them, oxygen has effects of disinfection by or sterilization by oxidation.

An inventor of this invention has proposed up to now gas mist pressure bathing systems, in which oxygen or carbon dioxide are efficiently dissolved in the liquid to turn out a gas mist to be supplied into a living body covering member which covers the skin and mucous membrane of the living body, and caused to be absorbed into the skin and mucous membrane, so that physiological actions of their gases can be influenced effectively over to the living body.

This prior gas mist pressure bathing is performed as in following procedures.
(1) Firstly, the living body covering member is set on an optional position of the living body, and an inside of the living body covering member is sealed.
(2) Subsequently, the gas mist is generated and supplied into the inside of the living body covering member.
(3) Under maintaining prescribed conditions (pressure, temperature, moisture and others) for a predetermined time, the gas mist pressure bathing is performed.

SUMMARY OF THE INVENTION

Problems That the Invention is to Solve

However, the above mentioned prior gas mist pressure bathing system has been involved with such problems that since, due to body temperature, the inside of the member covering the skin and mucous membrane of the living body heightens the temperature, the mist therein is much evaporated, and absorption efficiency of the gas mist from the skin and mucous membrane is lowered.

In view of the above mentioned circumstances, the present invention is to provide such a gas mist pressure bathing method and a gas mist pressure bathing system, in which the living body covering member is made double, and supply of the gas mist is divided into plural turns for improving absorption efficiency of the gas mist into the skin and mucous membrane of the living body.

Means for Solving the Problems

For solving the above mentioned problems, the invention is to provide such a gas mist pressure bathing method of causing, carbon dioxide or oxygen, or a mixed gas (called as "gas" hereafter) of carbon dioxide and oxygen and a liquid which are pulverized and dissolved to turn out a mist (called as "gas mist" hereafter) at concentration of not less than a predetermined value, to contact the skin or mucous membrane of the living body, and having a first cover placed inside and a second cover placed outside of the first cover to substantially seal the inside of the first cover, and preparing (a) a first step of covering the skin and mucous membrane of the living body, and supplying the gas mist and the gas mixed with this gas mist for a predetermined time into a space of at least the first cover of the living body covering member, the gas mist being supplied from the gas mist generation means, (b) a second step of discharging the gas mist and the gas from any one of the first cover and the second cover or from both, and (c) a third step of supplying the gas mist and the gas for the predetermined time into the first cover and the second cover from the gas mist generation means, and setting air pressure in at least the second cover to be within a predetermined range, and characterized by repeating the first to third steps in multiple turns.

By the way, the invention refers it as "pulverizing and dissolving" to pulverize the liquid into fine liquid drops, and cause to contact and mix with gas (carbon dioxide or oxygen, or the mixed gas of carbon dioxide and oxygen).

In the above mentioned gas mist pressure bathing method, it is also sufficient to provide a fourth step after the third step for discharging the gas mist from the inside of the living body covering member.

Further, in the first step and the third step, it is ideal to control environments in the first cover or the second cover to be within the ranges of predetermined values, based on one or plural sensors disposed within the first cover or second cover for measuring temperature, concentration of oxygen, concentration of carbon dioxide, or moisture.

Predetermined ranges of air pressure in the first cover and the second cover in the third step are desirable to be 1.01 to 2.5 air pressure.

For solving the above mentioned problems, the invention is to provide such a gas mist pressure bathing system of causing carbon dioxide or oxygen, or a mixed gas (called as "gas" hereafter) of carbon dioxide and oxygen and a liquid pulverized and dissolved to turn out a mist (called as "gas mist" hereafter) at concentration of not less than a predetermined value, to contact the skin or mucous membrane of the living body, the system of the invention being furnished with a gas supply means of supplying the above mentioned gas, a gas mist generation means of generating the above mentioned gas mist with the gas supplied from the gas supply means and a liquid stored inside and supplying the gas mist under a condition of mixing the gas, and a living body covering member which is a cover of covering the skin and mucous membrane of the living body and formed with a space for sealing inside the gas mist supplied from the gas mist generating means and the gas, characterized by furnishing a first cover placed inside and a second cover placed outside of the first cover and substantially sealing the inside of the first cover wherein a covering region of the first cover is narrower than that of the second cover, and by repeating to contact the gas mist to the covering region of the first cover, and thereafter to contact the gas mist to the covering region of the first cover and that of the second cover, thereby to improve skin-pass absorption efficiency of the gas mist.

The above mentioned gas mist pressure bathing system is also enough to furnish manometers of measuring pressure within the first and second covers and a control means of controlling air pressure within the first and second covers to be within predetermined values on the basis of the measured values of the manometers. Further, it is suitable to control environments in the first cover or the second cover to be within predetermined values, based on one or plural sensors disposed within the first cover or second cover for measuring temperature, concentration of oxygen, concentration of carbon dioxide, or moisture.

The first cover of the living body covering member has a shape of releasing the inside depending on the opening. Otherwise, this first cover of the living body covering member has such a shape of the inside being closed.

It is preferable to further dispose any one or a plurality of the sensors within the living body covering member for measuring temperature, concentration of oxygen, concentration of carbon dioxide, or moisture.

Further, the first cover desirably includes a hand palm or a foot sole in the covering region.

The above mentioned liquid is preferably any one or plural combination of water, ionic water, ozone water, physiological salt solution, purified water, or sterilized and purified water. And it is desirable to further contain any one or plural combination of menthol, vitamin E, vitamin C derivative, retinol, anesthetic agent, cyclodextrin, photo catalyst, complex of photo catalyst and apatite, hyaluronic acid, coenzyme Q10, seed oil, propolith, citric acid, ethanol, chlorhexidine gluconate, amphoteric surface active agent, benzalkonium chloride, alkyl diamino etherglycine acetate, sodium hypochlorite, peracetic acid, sodium sesquicarbonate, silica, povidone-iodine, sodium hydrogen carbonate, carbonate spring agent of high concentration, anti-allergic agent, anti-inflammatory agent, anti-febrile agent, anti-fungus agent, anti-influenza virus agent, influenza vaccine, steroid agent, anti-cancer agent, anti-hypertensive agent, cosmetic, or trichogen.

Based on the control means, gas is intermittently supplied from the gas supply means into the gas mist generation means to effect interval pressurization on the living body covering member.

A size of the mist supplied from the gas mist generating means into the living body cover member is suitably not larger than 10 μm.

Further on, there may be provided an electric charge giving means for giving an electric charge to the mist supplied by the gas mist generating means. At this time, the electric charge is preferably minus.

The gas mist generating means has desirably a gas mist supply pipe for supplying the gas mist and gas into the living body pressure bathing cover, and this gas mist supply pipe is furnished with a filter for removing liquid drops attaching to the inside of the pipe. Further, the gas mist supply pipe is composed of a cornice shaped pipe over a whole or at one part of the gas mist supply pipe. The cornice shaped pipe is formed with a groove in a shaft direction. In addition, this gas mist supply pipe is provided with a check valve.

The first cover has a gas mist supply port for receiving supply of the gas mist and gas from the gas mist generation means, and this gas mist supply port is provided with a check valve. When the inside of the first cover is substantially sealed, the second cover is also provided with the gas mist supply port for supplying the gas mist and gas from the gas mist generation means, and this gas mist supply port is provided with the check valve.

The control means stops gas supply from the gas supply means when pressure value within the living body covering member exceeds a predetermined value.

Effects of the Invention

Depending on the gas mist pressure bathing method and the gas mist pressure bathing system of the present invention, the skin and mucous membrane of the living body sweated and made easily absorb the gas mist is caused to contact the gas mist under an optimum condition, and effects of the gas mist pressure bathing can be heightened.

BRIEF DESCRIPTION OF THE DRAWINGS

FIG. 1 A flow chart for explaining the gas mist pressure bathing method depending on the present invention;

FIG. 2 A generally schematic view of the gas mist pressure bathing system depending on the first embodiment of the invention;

FIG. 3 A typical view in cross section showing the structure of the gas mist generator in the gas mist pressure bathing system of FIG. 1;

FIG. 4 A perspective view in cross section of the gas mist generator seeing from an arrow A direction of FIG. 3;

FIG. 5 A perspective view in cross section of the gas mist generator seeing from an arrow B direction of FIG. 3;

FIG. 6 A partially enlarged cross sectional view of the gas mist generator in the gas mist pressure bathing system in FIG. 1;

FIG. 7 A typical view showing the example of the gas mist supply pipe connecting the gas mist generator to the living body pressure bathing cover of the invention;

FIG. 8 A perspective view in cross section of the gas mist supply pipe shown in FIG. 7;

FIG. 9 A flow chart for explaining the gas mist pressure bathing method depending on the first embodiment of the invention;

FIGS. 10A-10D Typical view showing examples of shapes of the living body pressure bathing covers in the gas mist pressure bathing system depending on the first embodiment of the invention;

FIG. 11 A typical view (No. 1) showing an example of the shape of the living body pressure bathing cover in the gas mist pressure bathing system depending on the second embodiment of the invention;

FIG. 12 A flow chart for explaining the gas mist pressure bathing method depending on the second embodiment of the invention;

FIGS. 13A-13D Typical view (No. 2) showing examples of shapes of the living body pressure bathing covers in the gas mist pressure bathing system depending on the second embodiment of the invention;

FIG. 14 A generally schematic view of the gas mist pressure bathing system depending on the third embodiment of the invention;

Figure 15:
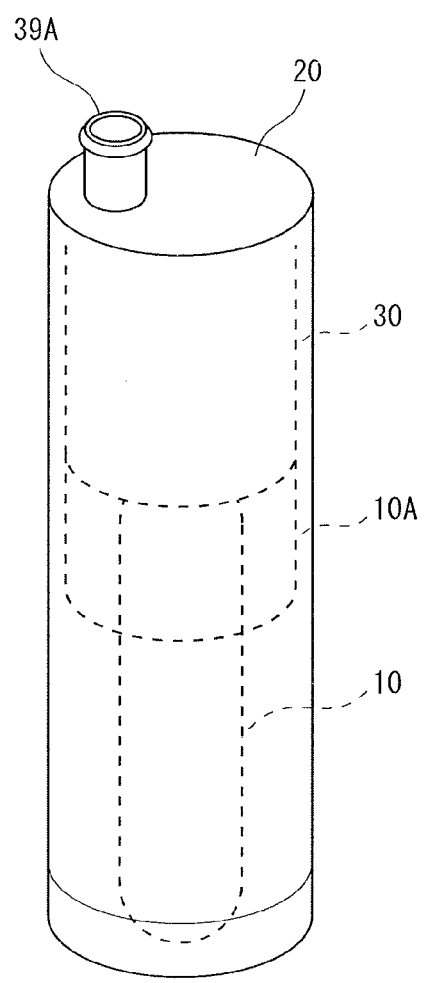
Figure 16A:
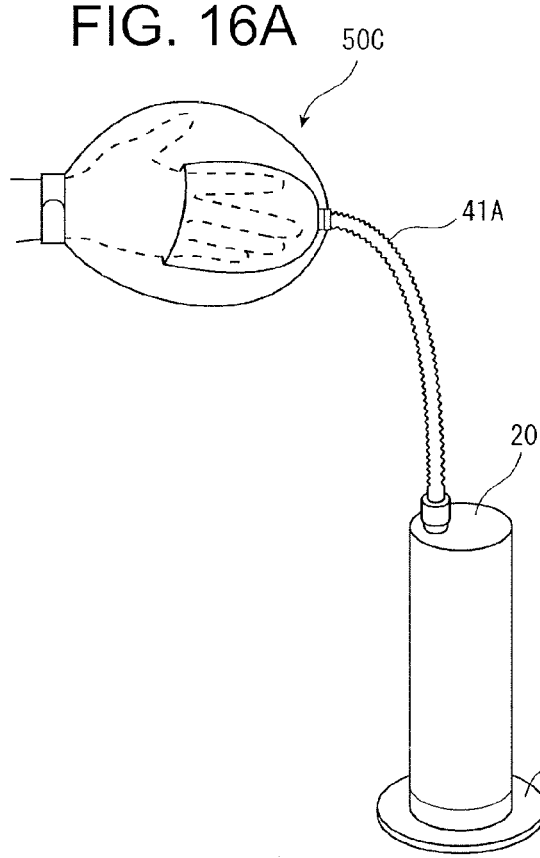
Figure 16C:
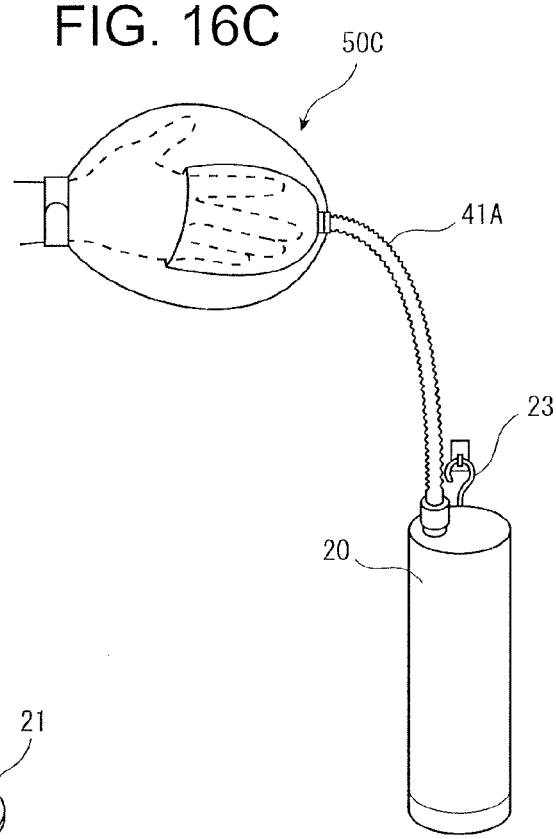
Figure 16B:
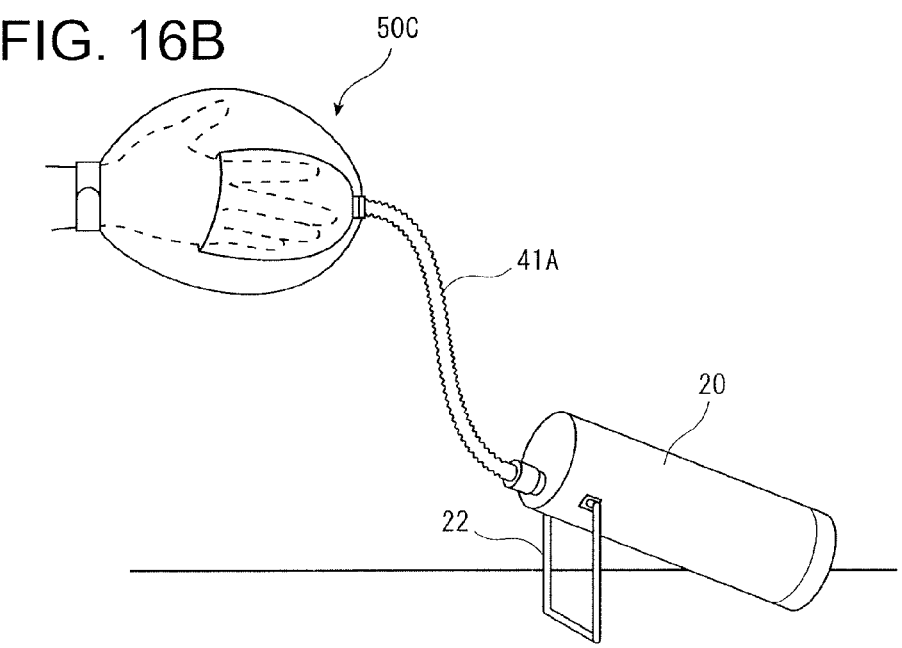

FIG. 15 A typical view showing a general appearance when housing the gas supply means and the gas mist generator in a case; and FIGS. 16A-16C Typical view showing examples of using the cases shown in FIG. 15.

EMBODIMENTS FOR PRACTICING THE INVENTION

In the following description, explanations will be made to embodiments of this invention, referring to the attached drawings.

The invention makes use of temperature-rise within the living body covering member owing to body-temperature, which has been one of prior problems as having mentioned above for taking effectively gas mist pressure bathing. That is, the invention makes a double structure having an inner cover and an outer cover of the living body covering member sealed with the gas mist, in which the inner cover is used for causing the gas mist to locally contact the skin or the mucous membrane of the living body, and the outer cover is used as a pressure controlling cover for absorbing the gas mist.

For the living body to absorb the gas mist from the skin or the mucous membrane, three routes are mainly present. One of them is called as "pore-pass quality", which is such a route absorbed from pores existing in a cuticle into a cortical layer through follicular or sebaceous gland. A second is called as "cuticle-pass quality", which is such a route gradually penetrating into a lower layer from a stratum corneum of the cuticle. A third is called as "sweat gland-pass quality" from the sweat gland existing in the cuticle into the cortical layer.

In a human body, many sweat glands exist from skin deep cortical layers over subcutaneous tissues. The sweat glands are divided into small sweat glands (eccrine gland) and large sweat glands (apocrine gland), and in particular, the small sweat glands are many in the hand palm and the foot sole, and are told as existing 2000000 to 5000000 pieces.

The sweat gland mainly works to secrete sweat for keeping the body temperature constant, but as said above, also largely concerns cutaneous absorption of materials. When skin temperature rises, the sweat is secreted to humidify the skin. Then, a protein combination of the stratum corneum is loosened to make subcutaneous penetration easy, so that the sweat glands or the pores are concurrently widened, blood penetration is accelerated thereby, and the gas mist absorption is carried out very efficiently.

Therefore, the invention composes the living body covering member with double covers of the inner cover (first cover) and the outer cover (second cover), and attaches to the living body. The region of the living body for attaching the inner cover includes parts having many sweat glands existing in the palms or the soles. The outer cover attaches to substantially seal the whole of the inner cover.

Showing in FIG. 1, as a first step (Step S1), the gas mist and gas mixed in this gas mist are supplied into at least the inner cover for a predetermined time. Subsequently, as a second step (Step S2), the gas mist and gas are discharged from any one or both of the inner cover and the outer cover, and further, as a third step (Step S3), the gas mist and gas are supplied into the inner cover and the outer cover for the predetermined time, and the air pressure within at least the second cover is brought to be in the predetermined range. By repeating these steps over plural turns, sweating by temperature rise within the cover as well as skin-pass absorption as checking the gas mist evaporation are repeated, so that the gas mist is caused to be absorbed at high efficiency.

That is, by utilizing rise of temperature within the living body covering member owing to the body-temperature together with lapse time, the sweat gland at the covered range of the living body is made opened to sweat out. When the pressure value in the living body covering member rises under a condition of sweating at the covered range, the skin-pass absorption is much smoothed. On the other hand, since the gas mist is gasified in company with temperature rising within the living body covering member, the step of supplying the gas mist is repeated, and the inside of the living body covering member is filled with the gas mist of high concentration. The sweat gland is thereby opened and the covered range under the sweating condition is contacted with the gas mist of the high concentration, so that skin-pass absorption of the gas mist is enabled at high efficiency.

In the following, more concrete explanations will be made to practicing examples.

First Embodiment

FIG. 2 is the generally schematic view of the gas mist pressure bathing system depending on the first embodiment of the invention. Showing in FIG. 2, the gas mist pressure bathing system of this embodiment is composed of a gas supply means 10 for supplying oxygen, carbon dioxide, or the mixed gas of oxygen and carbon dioxide (called as merely "gas" hereafter), a gas mist generator 30 as a gas mist generation means, a living body gas pressure bathing cover 50 as a living body covering member for sealing inside the supplied gas mist, and a control device 60 as a control means.

The gas supply means 10 supplies gas to a later mentioned connection part 31 of the gas mist generator 30. For example, a gas bomb of a cartridge system, a cassette bomb or a gas container of high pressure for official uses are also sufficient. The gas supply means 10 is desirably attached with a regulator for adjusting gas pressure, though not showing.

The gas mist generator 30 previously stores inside the liquid, generates the gas mist by pulverizing and dissolving the liquid and gas by high speed flowing of the gas supplied from the gas supply means 10, further mixes the gas, and supplies the gas mist into the living body pressure bathing cover 50.

FIG. 3 is the typical view in cross sectional showing the structure of the gas mist generator 30. FIG. 4 is the perspective view in cross section of the gas mist generator 30 seeing from an arrow A direction of FIG. 3. By the way, FIG. 4 omits a wall part and the connection part 31 in the front side of a liquid storage 33. FIG. 5 is the perspective view in cross section seeing from the arrow B direction of FIG. 3.

As showing in these Figures, the gas mist generator 30 has the connection part 31 connected with the gas supply means 10, a diverging part 32 of branching the gas flowing from the connection part 31, a liquid storage 33 of storing the liquid, a nozzle 34 of discharging one-side gas flow branched by the diverging part 32, a liquid suction pipe 35A of sending the liquid to the front end of the nozzle 34, a baffle (collision member) 36 of colliding the liquid blown up by the gas flow discharged from the nozzle with this baffle, a confluent part 37 of joining the generated gas mist with the gas from an upward side, a gas introduction part 38 of leading the other side gas flow branched by the diverging part 32 until the confluent part 37, and a gas mist discharge part 39 of collecting and discharging the generated gas mist, and those members are integrally formed.

To the connection part 31, the gas supply means 10 is connected directly, or via a gas code. The connection part 31 has such as a structure enabling to connect, by one touch, the gas supply means 10 or a gas code connected to the gas supply means 10, and in accordance with the gas supply means 10 to be connected, various forms may be employed.

The gas supplied from the gas supply means 10 via the connection part 31 is branched into two routes at the diverging part 32. One of them directs to the nozzle 34, while the other to the gas introduction part 38. The gas having directed to the nozzle 34 is discharged out of a front end open 34A of the nozzle. On the other hand, the gas to the gas introduction part 38 is guided to the confluent part 37.

The liquid storage 33 has been stored and sealed with a predetermined liquid in advance when having built at a stage of setting up the system of this invention. When using, this liquid storage is opened to perform the gas mist pressure bathing. Herein, as the liquid stored in the liquid storage 33, it is preferable to employ water, ionic water, ozone water physiological salt solution, purified water or sterilized and purified water. Further, these liquids are sufficient to contain medicines useful to users' diseases or symptom. As the medicines, for example, listed are anti-allergic agent, anti-inflammatory agent, anti-febrile agent, anti-fungus agent, anti-influenza virus agent, influenza vaccine, steroid agent, anti-cancer agent, or anti-hypertensive agent, cosmetic, or trichogen. Further, these liquids are further possible to generate synergistic effects by coupling with a gas physiological action with single or plurality of menthol having a cooling action; vitamin E accelerating circulation of the blood; vitamin C derivative easily to be absorbed to a skin tissue and having a skin beautifying effect; retinol normalizing a skin heratinizing action and protecting the mucous membrane; anesthetic agent moderating irritation to the mucous membrane; cyclodextrin removing odor; photocatalysis or a complex of photocatalysis and apatite having disinfection and anti-phlogistic; hyaluronic acid having excellent water holding capacity and a skin moisture retention effect; coenzyme Q10 activating cells and heightening immunization; a seed oil containing anti-oxidation and much nutrient; or propolith having anti-oxidation, anti-fungus, ant-inflammatory agent, pain-killing, anesthetic, and immunity. Otherwise, the liquid may be added with ethanol, gluconic acid chlorohexizine, amphoteric surface active agent, benzalkonium chloride, alkyldiamino ether glycin acetate, sodium hypochlorite, acetyl hydroperoxide, sodium sesqui-carbonate, silica, povidone-iodine, sodium hydrogen carbonate. In addition, carbonate spring of high concentration may be added (examples of organic components are sulfate, carbonate, or sodium dichloroiso-cyanurate).

At the bottom center of the liquid storage 33, the nozzle 34 is placed. This nozzle 34 protrudes from the bottom of the liquid storage 33, and is squeezed in diameter toward the baffle 36 to be formed almost as a circular cone. The nozzle 34 is connected, at its base end, to one side of the diverging part 32, and the nozzle 34 enables to discharge gas from its front end open 34A.

Figure 3:
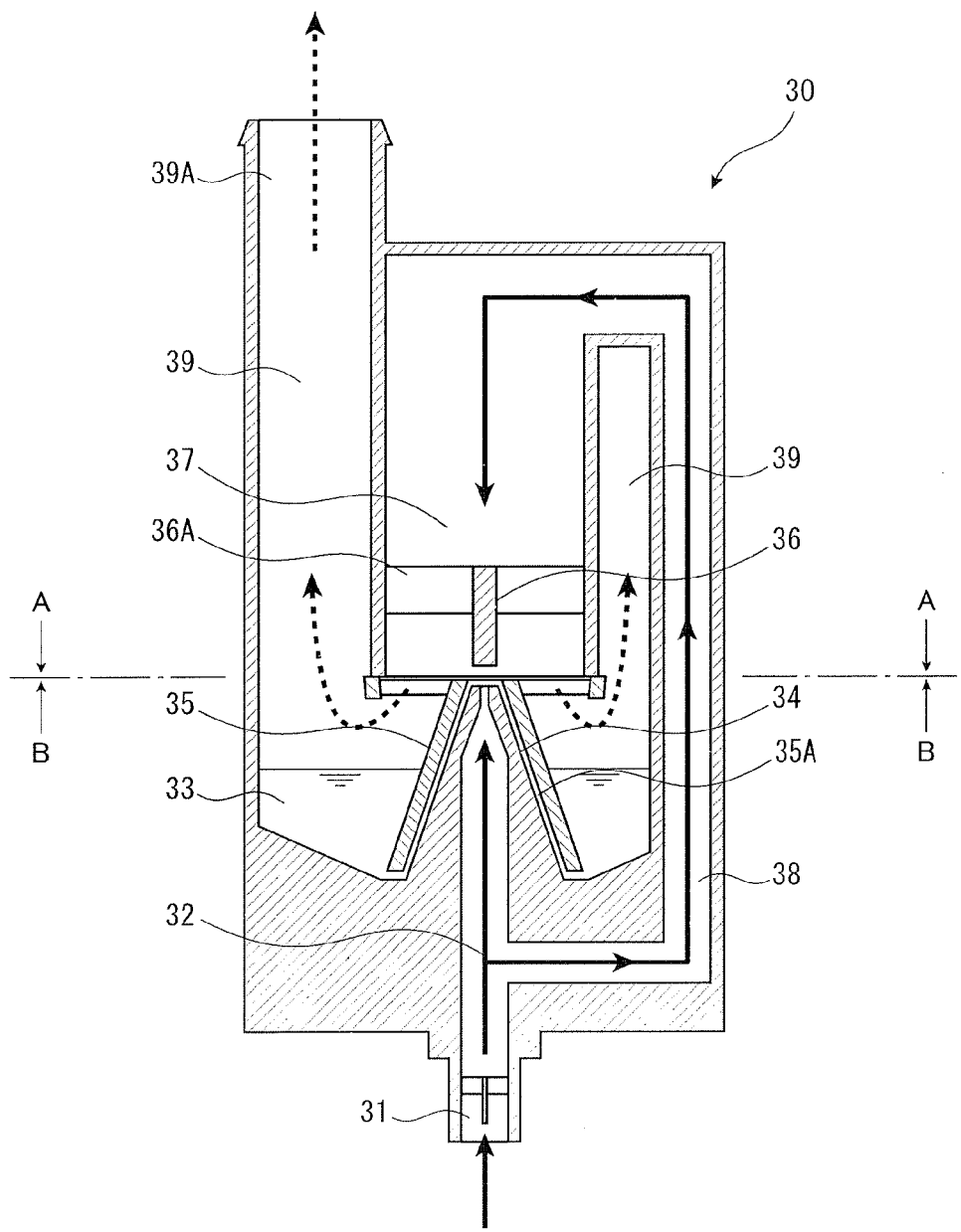
Figure 4:
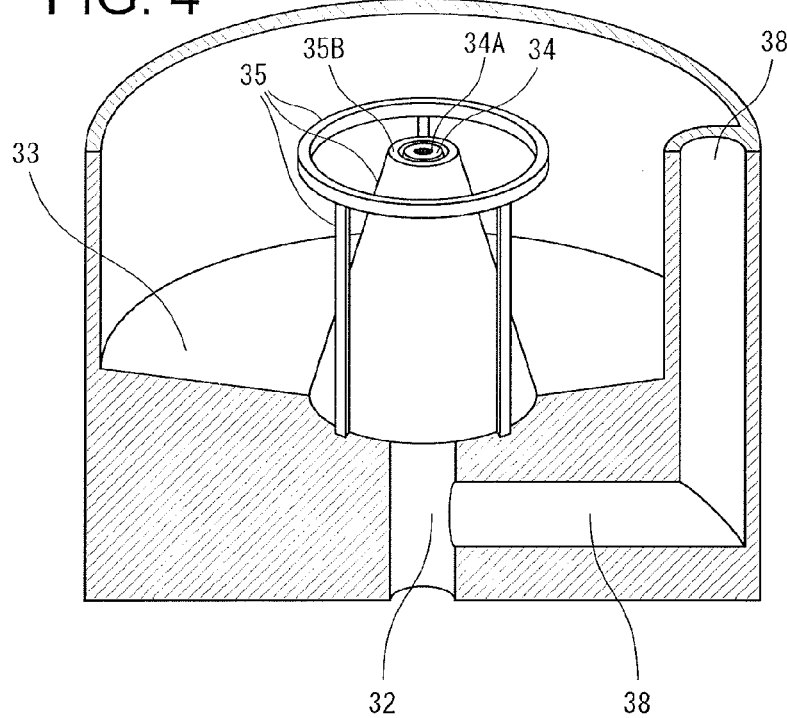
Figure 5:
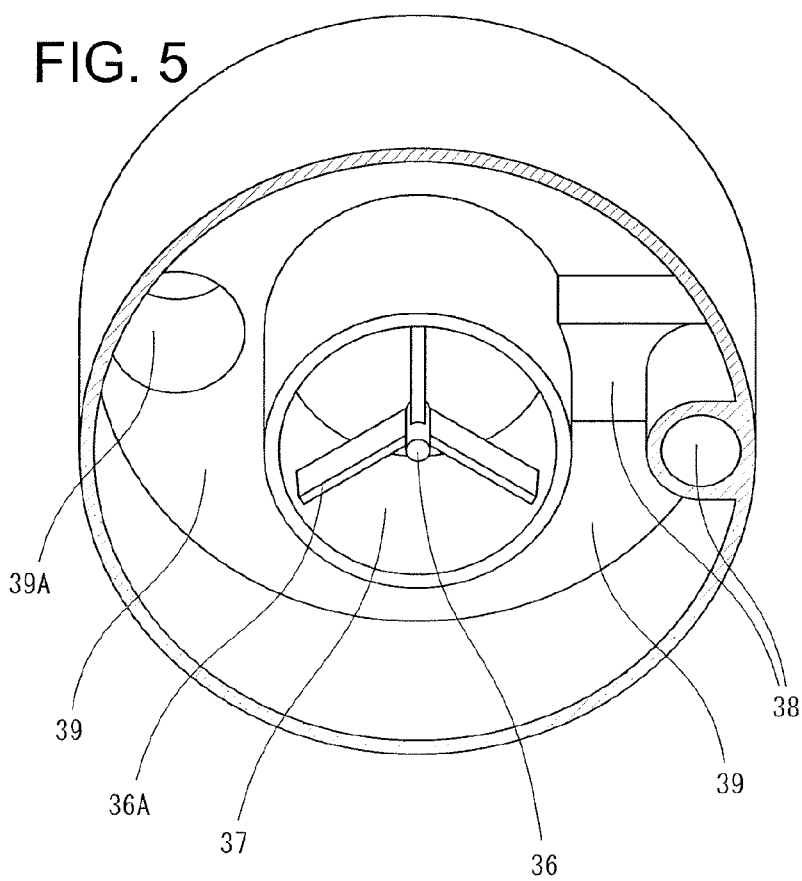

The liquid suction pipe 35A is formed between the outer circumference of the nozzle 34 and a liquid suction pipe-forming member 35 of the almost circular cone being larger by one turn than the nozzle 34. That is, as shown in FIG. 3, by positioning as covering the liquid suction pipe-forming member 35 over the nozzle 34, a liquid suction pipe 35A is defined between the outer circumference of the nozzle 34 and the inner circumference of the liquid suction pipe-forming member 35. Although having omitted to show, since a minute nail shaped projection is provided at a base end (the lower part of the almost circular cone part) of the liquid suction pipe-forming member 35, a space is defined on the bottom between a base of the liquid suction pipe-forming member 35 and the bottom of the liquid storage 33, and from this space the liquid stored in the liquid storage 33 is sucked up by the liquid suction pipe 35A. In addition, the front end part 35B of the liquid suction pipe-forming member 35 opens nearly the front end open 34A of the nozzle 34, and the liquid sucked up by the liquid suction pipe 35A collides with the gas flow discharged from the nozzle 34.

The liquid sucked up by the liquid suction pipe 35A collides with the gas flow discharged from the nozzle 34 and is blown up, struck against the baffle 36 placed in opposition to the front end open 34A of the nozzle 34 and crashed to turn out the gas mist. Herein, the baffle 36 is fixed to the inside wall of the confluent part 37 by a baffle supporter 36A, but may be fixed to a liquid suction pipe-forming member 35.

On the other hand, the gas branched at the diverging part 32 into the gas introduction part 38 gets to the confluent part 37 following the gas introduction part 38. The gas introduction part 38 is such a guiding path which passes the side face of the inside of the gas mist generator 30 from the diverging part 32 equipped at the lower part of the gas mist generator 30 and goes toward an upper part, and this gas introduction part 38 is formed integrally in the gas mist generator 30. The confluent part 37 is made of a cylindrical member disposed as encircling the baffle 36 above the front end open 34A of the nozzle 34, and communicates with the gas introduction part 38. Accordingly, the gas branched at the diverging part 32 and guided to the gas introduction part 38 confluents with the gas mist generated in the confluent part 37 at the upper part, and pushes out the gas mist toward a gas mist discharge part 39 formed around the cylindrical confluent part 37.

The gas supplied from the gas introduction part 38 into the confluent part 37 can be controlled in supply pressure owing to the size of a diameter of the gas introduction part 38. By controlling gas supply pressure, the gas mist supplying amount of the gas mist generator 30 is also can be controlled. Further, concentration of the gas mist (mist concentration in gas) or grain sizes of the mist can be also controlled by the diameter size in the gas introduction part 38.

A gas mist discharge part 39 is a space formed around the cylindrical confluent part 37, collecting the gas mist driven out from the confluent part 37 by the gas coming from the gas introduction part 38 and discharging the gas mist together with the gas. The gas mist driven out into the gas mist discharge part 39 is discharged into the living body pressure bathing cover 50 from the gas mist discharge port 39A opening at the upper part of the gas mist generator 30. An interval between the gas mist discharge port 39A and the living body pressure bathing cover 50 is connected by a gas mist supply pipe 41.

The gas mist generator 30 may be made such a structure which is able to displace a region including the at least liquid storage 33 and to replace another new liquid storage 33. That is, the gas mist generator 30 is made an assembling system and a replacing part including the liquid storage 33 is set up with another region, thereby enabling to accomplish a gas mist generator 30 integrating with the gas introduction part 38. Thus, if making the liquid storage 33 replaceable, the liquid storage 33 may be disposable enabling to keep hygiene. By making the liquid storage 33 replaceable, it is possible to omit a structure of supplementing the liquid into a liquid suction pipe 35A and to realize a device to be compact. By the way, the above mentioned gas mist generator 30 is desirably treated with sterilization when having built at a stage of setting up the system of this invention.

Figure 6:
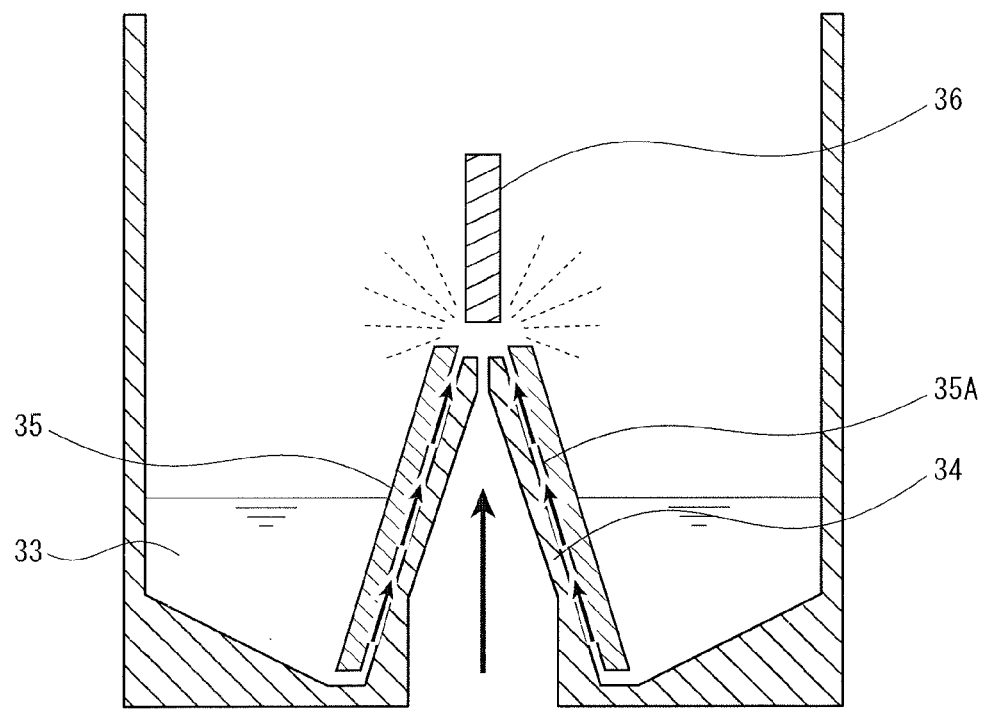

The above mentioned gas mist generator 30 generates the gas mist as follows. When gas is supplied into the nozzle 34 from the gas supply means 10, since the nozzle 34 is reduced in diameter toward the front end as shown in FIG. 6, the gas increases the flowing speed and is discharged. The liquid in the liquid storage 33 is sucked up within the liquid suction pipe 35A owing to negative pressure caused by air flow of this time, is blown up by gas at the front end part 35B of the liquid suction pipe 35A, and collides against the baffle 36, so that the gas mist is generated. Desirably, the diameter of the mist generated by this collision is fine, and concretely, best is not larger than 10 µm. The thus finely pulverized mist can display effects of minus ion.

The gas further passes through the diverging part 32 and is guided to the confluent part 37 from the gas introduction part 38, and heightens the discharging pressure of the generated gas mist. The generated gas mist is mixed with gas from the diverging part 32 and discharged from the gas mist discharge port 39A into the living body pressure bathing cover 50 via a later mentioned gas mist supply pipe 41.

Figure 7:
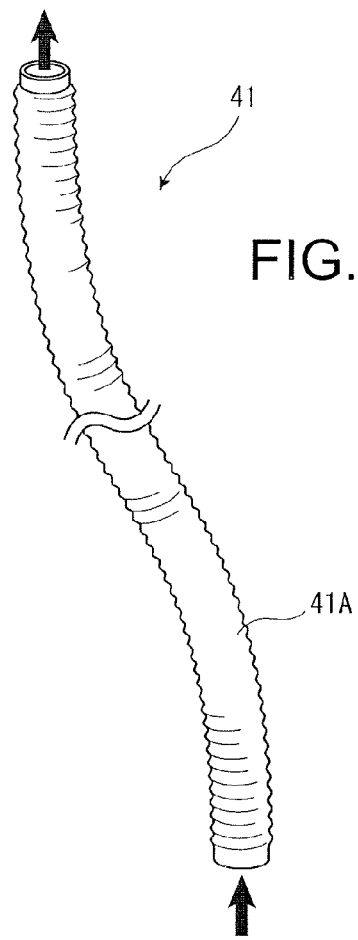
Figure 8:
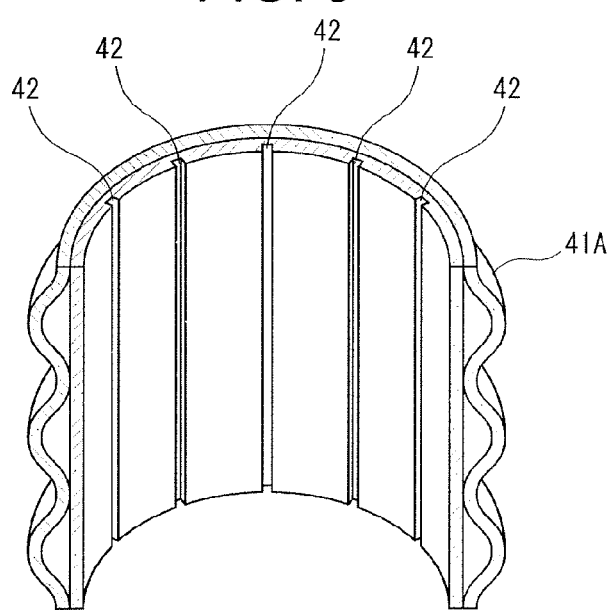

The gas mist supply pipe 41 is desirably composed wholly or partially with a soft and cornice shaped pipe 41A of large diameter as shown in FIG. 7, and this is freely bent or expanded and contracted so that a user's action is not limited. In addition, as shown in FIG. 8, the cornice shaped pipe 41A is formed inside with grooves 42 in an axial direction of the pipe. FIG. 8 illustrates the inside of the cornice shaped pipe 41A is smooth, but may be formed to be cornice shape as the outside. Also in such a case, by forming the grooves 42, the liquefied gas mist is recovered.

The gas mist supply pipe 41 is provided inside with a check valve to avoid back flows of the gas mist and gas. Further, though not showing, the gas mist supply pipe 41 is preferably provided with a droplet removing filter to remove extra droplets attaching to the inside of the pipe.

Figure 2:
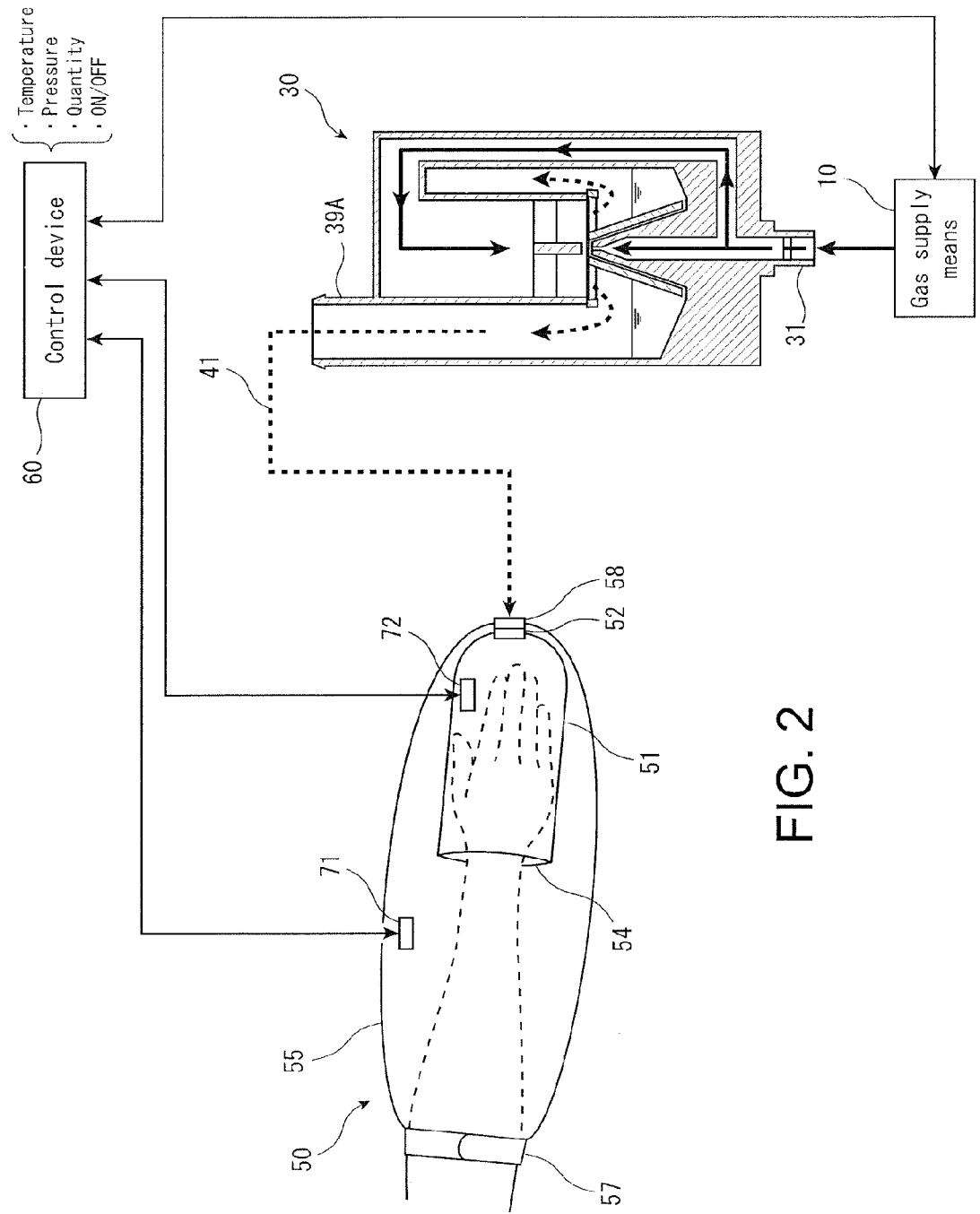

The living body pressure bathing cover 50 is such a cover which covers the skin and mucous membrane of the living body (in FIG. 2, as the example, a forearm of the human body), forming a space for sealing inside the gas mist and gas. The living body pressure bathing cover 50 is composed of a first cover (an inner cover) 51 positioned inside and a second cover (an outer cover) 55 positioned outside to cover the whole of the first cover 51 and enable to substantially seal. The living body pressure bathing cover 50 is preferably composed of pressure resistant, non-air permeable and non-moisture permeable materials, for example, a natural rubber, silicone rubber, polyethylene, polypropylene, polyvinylidene, polystyrene, polyvinylacetate, polyvinyl chloride, polyamide resin, polytetrafluoroethylene, and the like.

The inner cover 51 is a substantially bag-shaped cover for covering locally regions being high at absorption rate of the gas mist, and at the same time, functions as a heat insulating cover. That is, after temperature rises within the living body covering member 50 as time passes, the gas mist generated at room temperature and relatively low temperature is supplied, and the inner cover 51 is suitably composed with a heat insulating material not to soon rise. By attaching this inner cover 51, it is possible to avoid evaporation of the gas mist supplied during taking the gas mist pressure bathing. The inner cover 51 is attached to such regions of especially absorbing the gas mist, having many sweat glands and easily sweating as the palm or sole.

The inner cover 51 has a supply port 52 connected to the gas mist supply pipe 41 for introducing the gas mist and gas into the inside thereof. This supply port 52 is has a check valve for preventing back flows of the gas mist and gas, though not showing. An end of the inner cover 51 is here an opening 54. Accordingly, the gas mist and gas supplied into the inner cover 51 are also supplied into the outer cover 55 through the opening 54.

The outer cover 55 is larger than the inner cover 51, can cover the skin and mucous membrane of the living body and wholly the inner cover 51, and is formed almost as a bag. At an opening of the outer cover 55, a stopper 57 is furnished for enabling to attach to and detach from the living body, and for avoiding leaking the gas mist and gas sealed inside. The stopper 57 is suitably composed of, e.g., a face fastener of stretching property, or may have a string, rubber or their combination. Further, since the outer cover 55 necessitates a sealing property, the inside of the stopper 57 may be disposed with a material adhesive to the skin of the living body. This adhesive material is preferably, for example, a visco-elastic gel made of polyurethane or silicone rubber. Further this adhesive material is detachably used and exchangeable each time, if viscosity becomes weak.

Further, the outer cover 55 is provided with a connection part 58 for connecting a supply port 52 of the inner cover 51 and for connecting the inner cover 51 and the gas mist supply pipe 41 as closing the inside of the outer cover 55. Not showing, the outer cover 55 is suitably provided with a gas mist discharge port for discharging the gas mist and gas from the inside of the cover, or with a valve for controlling pressure of the inside of the cover. Pressure within the cover may be controlled manually, but automatic performance is desirable by a control device 60 together with supply control of the gas mist based on measuring values of a later mentioned manometer 71. A safety valve (escape valve) is desirably furnished for automatically opening the valve when the inside of the outer cover 55 comes above a fixed pressure value.

There has been shown such a structure, as an example, having the connection part 58 for connecting the supply port 52 of the inner cover 51, but if being able to supply the gas mist to the inner cover 51 as sealing the inside of the outer cover 55, any forms may be applied.

The outer cover 55 is installed with the manometer 71 for measuring pressure of the inside thereof. The control device 60 controls generation and supply of the gas mist, based on the measured values of the manometer 71 for keeping the pressure value within the outer cover 55 to be not less than 1 air pressure (more preferably, 1.01 to 2.5 air pressure). For example, supply of gas from the gas supply means 10 is adjusted or stopped, otherwise, the gas mist and gas are discharged from the inner cover 51 or from the outer cover 55. By the way, since the present embodiment uses the living body pressure bathing cover 50 under the condition where the inner cover 51 is released by the opening 54, the manometer 71 is enough with one provided within the outer cover 55. Further, as showing in FIG. 2, a temperature gage 72 may be installed for measuring temperatures within the inner cover 51 or the outer cover 55 (herein, within the inner cover 51). The control device 60 turns ON-OFF of supplying the gas mist from measuring values of the temperature gage 72.

As to others, there may be installed sensors within the living body pressure bathing cover 50 for measuring concentration of oxygen, concentration of carbon dioxide or moisture for controlling environments in the covers to be within respectively predetermined values by the control device 60.

The control device 60 is composed of a computer having CPU, memory and display. Various kinds of controls are performed such as control or ON-OFF switch of gas pressure supplied from the gas supply means 10, or ON-OFF switch of supplying the gas mist for carrying out the gas mist pressure bathing under an optimum condition. In particular, from the measuring values of the sensors of the manometer 71 or the temperature gage 72 installed in the living body pressure bathing cover, the respective means are controlled to keep the optimum condition within the living body pressure bathing cover 50 for taking the gas mist pressure bathing. When the pressure value in the living body pressure bathing cover 50 is higher than the predetermined value, such a structure of the system is suitably built to stop the gas supply of the gas supply means 10 by the control device 60. Incidentally, the above mentioned controls may be manual without using the control device 60.

Figure 9:
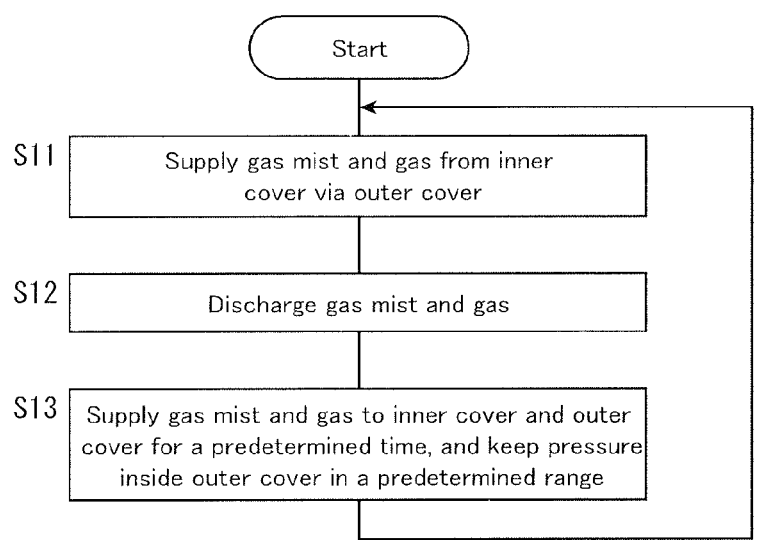

Following explanations will be made with FIG. 9 to the gas mist pressure bathing method using the gas mist pressure bathing system of the above mentioned embodiment.

At first, as a preparatory step, the sealed gas mist generator 30 is brought to under a usable condition as manners of opening the sealed gas mist generator 30 and connecting to the gas supply means 10. As to the living body pressure bathing cover 50, the inner cover 51 is attached to an optional part of the living body, and subsequently, the outer cover 55 is attached to cover the whole of the inner cover 51 for securing to the living body to substantially seal the inside.

Next, gas supply is started from the gas supply means 10 into the gas mist generator 30 to generate the gas mist by mixing gas and supply into the inner cover 51 for a predetermined time (Step S11). In the present embodiment, the gas mist and gas are also supplied into the outer cover 55 via the inner cover 51. By supplying the gas mist into the inner cover 51, the gas mist is locally contacted to regions of the living body easily absorbing the gas mist, or to such regions especially absorbing the gas mist. At this time, for safety, the control device 60 allows for supplying or discharge the gas mist and gas on the basis of the value of the manometer 71 such that the inside of the living body pressure bathing cover 50 is not brought above the predetermined pressure value.

The gas mists and gases within the inner cover 51 and the outer cover 55 are discharged (Step S12). In the present embodiment, the gas mist and gas are discharged outside from a gas mist discharge port (not shown) of the outer cover 55 or from the stopper 57.

Next, the gas mist and gas are supplied from the gas mist generator 30 into the inner cover 51 and the outer cover 55 for a fixed time (Step S13). In this embodiment, similarly to Step S11, the gas mist and gas are also supplied into the outer cover 55 via the inner cover 51. At this time, the control device 60 is controlled from the measured values of the manometer 71, such that air pressure in the inner cover 51 and the outer cover 55 is brought in the fixed range (more preferably, 1.01 to 2.5 air pressure). For safety, the control device 60 allows for supplying or discharging the gas mist and gas on the basis of the value of the manometer 71, such that the inside of the living body pressure bathing cover 50 is not brought above the predetermined pressure value.

If stopping supply of the gas mist and gas after maintaining the condition of Step S13, the gas mist and gas get away bit by bit from the inside of the outer cover 55 effected with pressure. Further, due to the body temperature, the temperature within the living body pressure bathing cover 50 heightens. Then, the operation again returns to Step S11. By repeating the above steps at plural turns (preferably, three turns), with respect to the skin and mucous membrane of the living body, sweating by temperature-rise in the cover and repeating the turn of the cutaneous absorption by suppressing evaporation of the gas mist, the gas mist can be absorbed at high efficiency.

By the way, in case the sealing property of the outer cover 55 is high or if necessary, it is sufficient to discharge the gas mist and gas in the outer cover 55 and the inner cover 51 after Step S13.

The above explanation has been made to the example of the man's forearm as the region to be carried out with the gas mist pressure bathing, but the present invention can be applied to various regions of the living body. In such cases, the living body pressure bathing cover 50 meeting an object region is employed for taking the optimum gas mist pressure bathing.

FIGS. 10A to 10D show examples of various shapes of the living body pressure bathing cover 50.

Figure 10A:
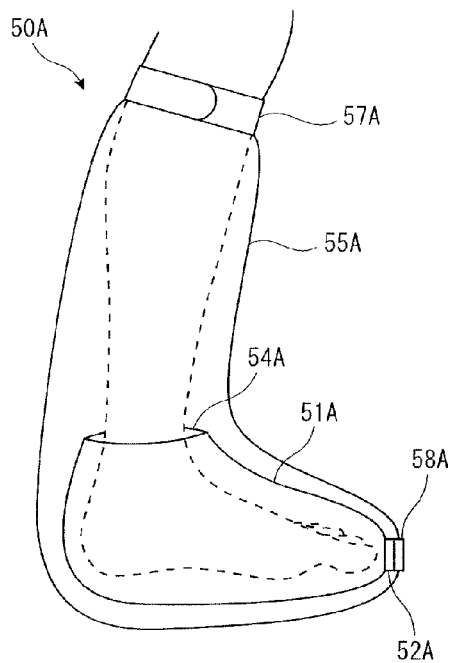

FIG. 10A is a living body pressure bathing cover 50A for a lower extremity (below the knee) of the human body. This living body pressure bathing cover 50A is composed of an inner cover 51A covering the whole of the foot and knee, and an outer cover 55A covering the part below the knee and the inner cover 51A. The inner cover 51A has a supply port 52A connecting to the gas mist supply pipe 41 for introducing inside the gas mist and gas. The inner cover 51A is an opening 54A at an end. The outer cover 55A has a stopper 57A and a connection part 58A, the stopper 57A enabling to attach to and detach from the living body and avoiding leakage of the gas mist and gas sealed inside, and the connection part 58A connecting the inner cover 51A to the gas mist supply pipe 41 while sealing the inside of the outer cover 55A by connecting the supply port 52A of the inner cover 51A and the gas mist supply pipe 41.

Figure 10B:
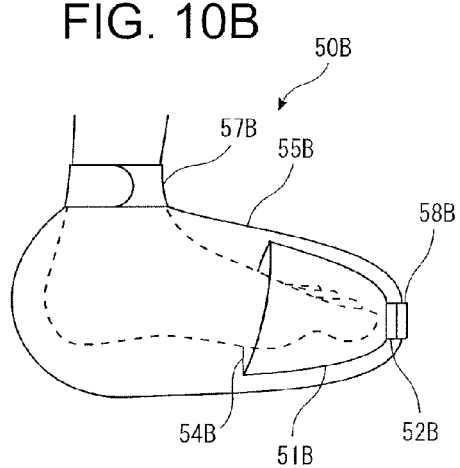

FIG. 10B is a living body pressure bathing cover 50B for a foot part of the human body. This living body pressure bathing cover 50B is composed of an inner cover 51B covering the foot toes, and an outer cover 55B covering the foot part and the inner cover 51B. The inner cover 51B has a supply port 52B connecting to the gas mist supply pipe 41 for introducing the gas mist and gas inside. The inner cover 51B is an opening 54B at an end. The outer cover 55B has a stopper 57B and a connection part 58B, the stopper 57B enabling to attach to and detach from the living body and avoiding leakage of the gas mist and gas sealed inside, and the connection part 58B connecting the inner cover 51B to the gas mist supply pipe 41 while sealing the inside of the outer cover 55B by connecting the supply port 52B of the inner cover 51B and the gas mist supply pipe 41.

Figure 10C:
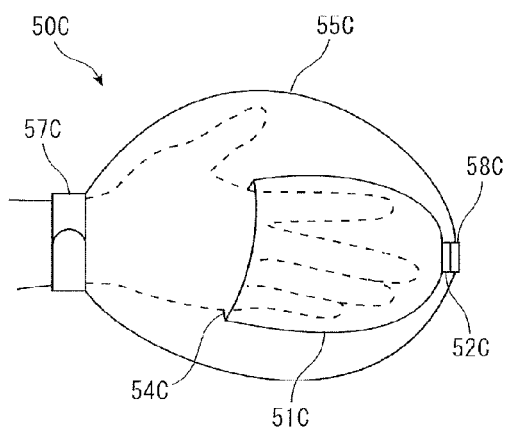

FIG. 10C is a living body pressure bathing cover 50C for a hand part of the human body. This living body pressure bathing cover 50C is composed of an inner cover 51C covering the hand fingers, and an outer cover 55C covering the hand part and the inner cover 51C. The inner cover 51C has a supply port 52C connecting to the gas mist supply pipe 41 for introducing the gas mist and gas inside. The inner cover 51C is an opening 54C at an end. The outer cover 55C has a stopper 57C and a connection part 58C, the stopper 57C enabling to attach to and detach from the living body and avoiding leakage of the gas mist and gas sealed inside, and the connection part 58C connecting the inner cover 51C to the gas mist supply pipe 41 while sealing the inside of the outer cover 55C by connecting the supply port 52C of the inner cover 51C and the gas mist supply pipe 41.

Figure 10D:
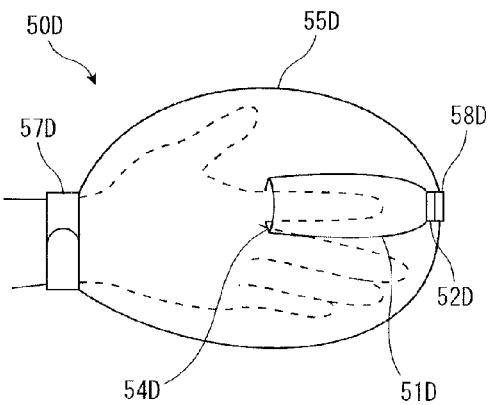

FIG. 10D is also a living body pressure bathing cover 50D for a hand part of the human body. This living body pressure bathing cover 50D is composed of an inner cover 51D covering the forefinger, and an outer cover 55D covering the hand part and the inner cover 51D. The inner cover 51D has a supply port 52D connecting to the gas mist supply pipe 41 for introducing the gas mist and gas inside. The inner cover 51D is an opening 54D at an end. The outer cover 55D has a stopper 57D and a connection part 58D, the stopper 57D enabling to attach to and detach from the living body and avoiding leakage of the gas mist and gas sealed inside, and the connection part 58D connecting the inner cover 51D to the gas mist supply pipe 41 while sealing the inside of the outer cover 55D by connecting the supply port 52D of the inner cover 51D and the gas mist supply pipe 41.

Second Embodiment

The above explanation has been made to the living body pressure bathing cover 50 where the inner cover 51 is opened by the opening 54, but the inner cover may be left as the inside being closed. The following explanation will be made to a living body pressure bathing cover 150 closed at the inner cover, referring to FIG. 11. Since the structure of the gas mist pressure bathing system is the same as the first embodiment excepting the living body pressure bathing cover 150, illustration and explanation thereof will be omitted.

The living body pressure bathing cover 150 is a cover which is such a cover for covering the skin and mucous membrane of the living body (in FIG. 11, as the example, a forearm of the human body) and forming a space for sealing the gas mist and gas. The living body pressure bathing cover 150 is composed of a first cover (an inner cover) 151 positioned inside and a second cover (an outer cover) 155 positioned outside to cover the whole of the first cover 151 and enable to substantially seal. The living body pressure bathing cover 150 is preferably composed of pressure resistant, non-air permeable and non-moisture permeable materials, for example, the natural rubber, silicone rubber, polyethylene, polypropylene, poly-vinylidene, polystyrene, polyvinyl acetate, polyvinyl chloride, poly amide resin, polytetra-fluoroethylene.

The inner cover 151 is a substantially bag-shaped cover for covering locally regions of the living body being high at absorption rate of the gas mist, and at the same time, functions as a heat insulating cover. Therefore, the inner cover 151 is suitably composed with a heat insulating material. By attaching this inner cover 151, it is possible to avoid evaporation of the gas mist supplied during taking the gas mist pressure bathing. The inner cover 151 is attached to such regions of the living body having many sweat glands and easily sweating as the palm or sole.

The inner cover 151 is connected to the gas mist supply pipe 41 and has a supply port 152 for introducing the gas mist and gas into the inside. This supply port 152 is has a check valve for preventing back flows of the gas mist and gas, though not showing. At an opening part of the inner cover 151, a stopper 153 is furnished for enabling to attach to and detach from the human body as well as for avoid leakage of the gas mist and gas sealed inside. The stopper 153 is sufficiently composed of an elastic face fastener, string or rubber.

The stopper 153 of the inner cover 151 may be strongly attached to the human body to such a degree of enabling to seal the inside of the inner cover 151, or lightly engaged with a rubber or the like. Further, not showing, the inner cover 151 is suitably provided with a gas mist discharge port for discharging the gas mist and gas from the inside of the cover, and with a valve for controlling pressure of the inside of the cover. Especially, a safety valve (escape valve) is desirably furnished for automatically opening the valve when the inside of the inner cover 151 comes above a fixed pressure value.

The outer cover 155 is larger than the inner cover 151, can cover wholly the skin and mucous membrane of the living body and the inner cover 151, and is formed almost as a bag. The outer cover 155 is connected to the gas mist supply pipe 41 and has a supply port 156 for introducing the gas mist and gas into the inside thereof. This supply port 156 is provided with the check valve for avoiding back flows of the gas mist and gas, though not showing. At an opening of the outer cover 155, a stopper 157 is furnished for enabling to attach to and detach from the living body and at the same time for avoiding leaking the gas mist and gas sealed inside. The stopper 157 is suitably composed of, e.g., the face fastener of stretching property, or may have a string, rubber or their combination. Further, since the outer cover 155 necessitates a sealing property, the inside of the stopper 157 may be disposed with a material adhesive to the skin of the living body. This adhesive material is preferably, for example, a visco-elastic gel made of polyurethane or silicone rubber. Further this adhesive material is detachably used and exchangeable each time or if viscosity becomes weak.

Further, the outer cover 155 is provided with a connection part 158 for connecting a supply port 152 of the inner cover 151 and for connecting the inner cover 151 and the gas mist supply pipe 41 as closing the inside of the outer cover 155. Not showing, the outer cover 155 is suitably provided with a gas mist discharge port for discharging the gas mist and gas from the inside of the cover, or with a valve for controlling pressure of the inside of the cover. Pressure within the cover may be controlled manually, but automatic performance is desirable by a control device 60 together with supply control of the gas mist based on measuring values of the manometer 71. The safety valve (escape valve) is desirably furnished for automatically opening the valve when the inside of the outer cover 155 comes above a fixed pressure value.

There has been shown such a structure, as an example, having the connection part 158 for connecting the supply port 152 of the inner cover 151, but if being able to supply the gas mist to the inner cover 151 as sealing the inside of the outer cover 155, any forms may be applied.

Figure 11:
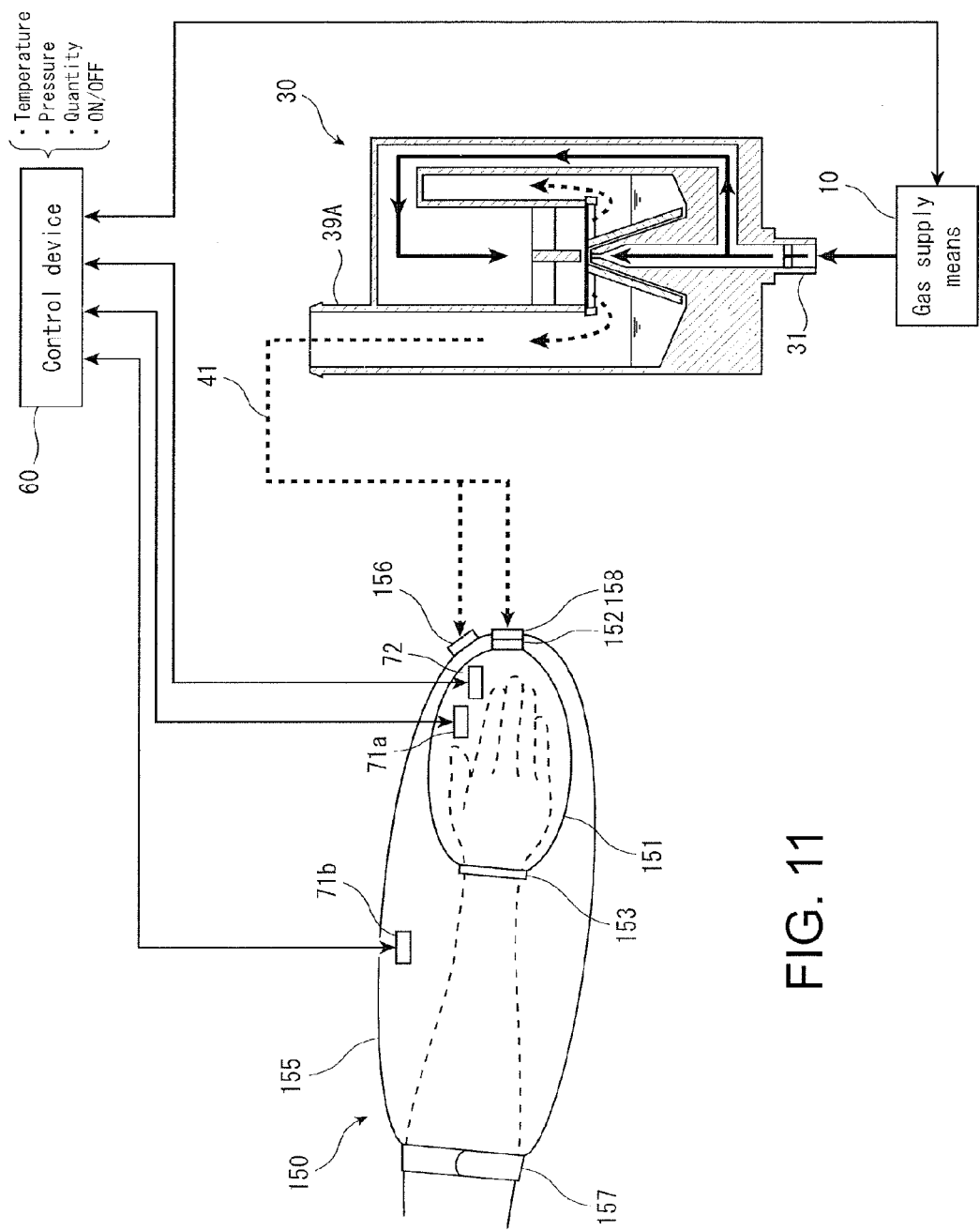

In the case of the living body pressure bathing cover 150 of the present embodiment, since the inner cover 151 and the outer cover 155 are independently structured respectively, it is preferable to furnish the respective manometers 71a, 71b to both covers 151, 155 as showing in FIG. 11. The temperature gage 72 may be furnished to the inner cover 151 only or to both of the inner cover 151 and outer cover 155.

Figure 12:
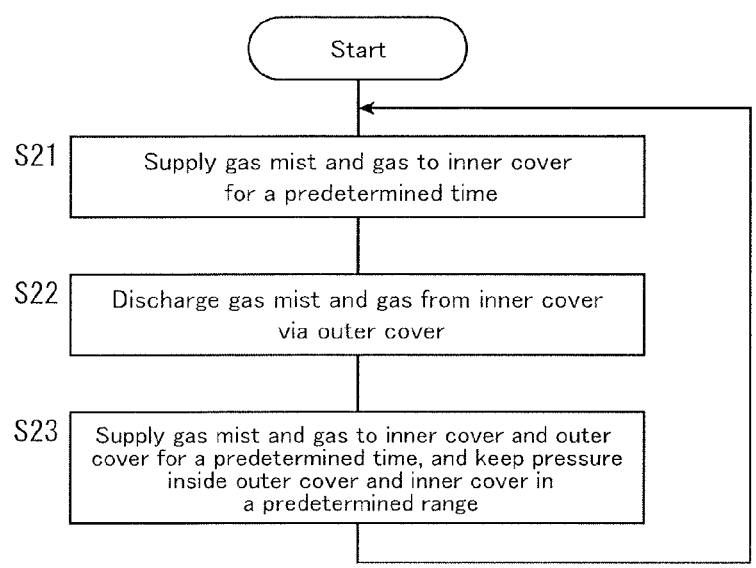

Following explanations will be made with FIG. 12 to the gas mist pressure bathing method using the gas mist pressure bathing system having the living body pressure bathing cover 150 of the present embodiment.

At first, as a preparatory step, the sealed gas mist generator 30 is brought to under a usable condition as manners of opening the scaled gas mist generator 30 and connecting to the gas supply means 10. As to the living body pressure bathing cover 150, the inner cover 151 is attached to an optional part of the living body, and subsequently, the outer cover 155 is attached to cover the whole of the inner cover 151 for securing to the living body to seat the inside.

Gas supply is started from the gas supply means 10 into the gas mist generator 30 to generate the gas mist by mixing gas and supply into the inner cover 151 for a predetermined time (Step S21). By supplying the gas mist into the inner cover 151, the gas mist is locally contacted to regions of the living body easily absorbing the gas mist or to such regions especially absorbing the gas mist. At this time, for safety, the control device 60 allows for supplying or discharging the gas mist and gas on the basis of the value of the manometer 71a, such that the inside of the living body pressure bathing cover 151 is not brought above the predetermined pressure value.

Next, the gas mist and gas within the inner cover 151 are discharged (Step S22). In this embodiment, the gas mist and gas are once discharged into the outer cover 155 from a gas mist discharge port (not shown) of the inner cover 151 or from the stopper 153, and after then, the gas mist and gas are discharged into the outer cover 155 from a gas mist discharge port (not shown) of the outer cover 155 or from the stopper 157. Otherwise, it is enough to only discharge the gas mist and gas within the inner cover 151 into the outer cover 155.

The gas mist and gas are supplied from the gas mist generator 30 into the inner cover 151 and the outer cover 155 for a fixed time (Step S23). At this time, the control device 60 is controlled from the measured values of the manometers 71a, 71b, such that air pressure in the inner cover 151 and the outer cover 155 is brought to in the fixed range (preferably, 1.01 to 2.5 air pressure). For safety, the control device 60 allows for supplying or discharging the gas mist and gas on the basis of the values of the manometers 71a, 71b such that the inside of the living body pressure bathing cover 150 is not brought above the predetermined pressure value.

The above explanation has been made to the example of the man's forearm as the region to be carried out with the gas mist pressure bathing, and FIGS. 13A to 13D show examples of various shapes of the living body pressure bathing cover 150.

Figure 13A:
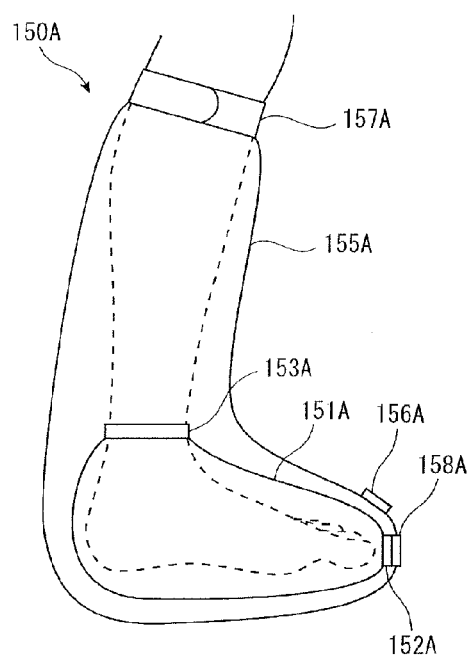

FIG. 13A is a living body pressure bathing cover 150A for a lower extremity (below the knee) of the human body. This living body pressure bathing cover 150A is composed of an inner cover 151A covering the whole of the foot and knee, and an outer cover 155A covering the part below the knee and the inner cover 151A. The inner cover 151A has a supply port 152A connecting to the gas mist supply pipe 41 for introducing inside the gas mist and gas. Further, the inner cover 151A has a stopper 153A enabling to attach to and detach from the living body and avoiding leakage of the gas mist and gas sealed inside. The outer cover 155A has a supply port 156A connecting to the gas mist supply pipe 41 for introducing the gas mist and gas into the inside. The outer cover 155A has a stopper 157A and a connection part 158A, the stopper 157A enabling to attach to and detach from the living body and avoiding leakage of the gas mist and gas sealed inside, and the connection part 58A connecting the inner cover 51A to the gas mist supply pipe 41 while sealing the inside of the outer cover 155A by connecting the supply port 152A of the inner cover 151A and the gas mist supply pipe 41.

Figure 13B:
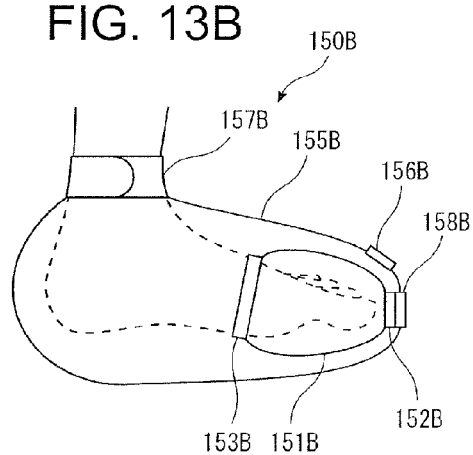

FIG. 13B is a living body pressure bathing cover 150B for a foot part of the human body. This living body pressure bathing cover 150B is composed of an inner cover 151B covering the foot toes and an outer cover 155B covering the foot part and the inner cover 151B. The inner cover 151B has a supply port 152B connecting to the gas mist supply pipe 41 for introducing inside the gas mist and gas. The inner cover 151B is provided with a stopper 153B at its opening enabling to attach to and detach from the living body and avoiding leakage of the gas mist and gas sealed inside. The outer cover 155B is provided with a supply port 156B connecting to the gas mist supply pipe 41 for introducing the gas mist and gas inside. The outer cover 155B is provided with a stopper 157B and a connection part 158B, the stopper 157B enabling to attach to and detach from the living body and avoiding leakage of the gas mist and gas sealed inside and the connection part 158B connecting the inner cover 151B to the gas mist supply pipe 41 while sealing the inside of the outer cover 155B by connecting the supply port 152B of the inner cover 151B and the gas mist supply pipe 41.

Figure 13C:
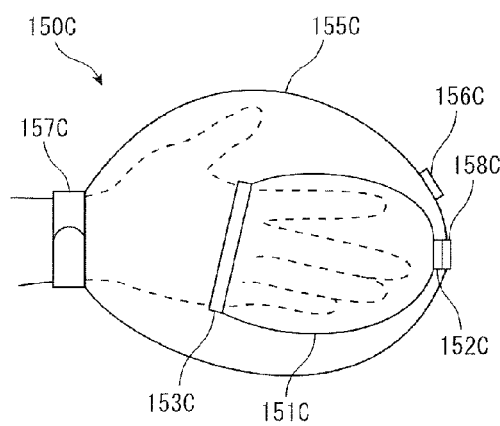

FIG. 13C is a living body pressure bathing cover 150C for a hand part of the human body. This living body pressure bathing cover 150C is composed of an inner cover 151C covering the forefinger, and an outer cover 155C covering the hand part and the inner cover 151C. The inner cover 151C has a supply port 152C connecting to the gas mist supply pipe 41 for introducing the gas mist and gas inside. The inner cover 151C is provided with a stopper 157C at its opening for enabling to attach to and detach from the living body and avoiding leakage of the gas mist and gas sealed inside. The outer cover 155C has a supply port 156C connecting to the gas mist connection pipe 41 for introducing the gas mist and gas inside. The outer cover 155C is provided with a stopper 157C and a connection part 158B, the stopper 157C enabling to attach to and detach from the living organ, and the connection part 158B connecting the inner cover 151B to the gas mist supply pipe 41 while sealing the inside of the outer cover 155C by connecting the supply port 152B of the inner cover 151C and the gas mist supply pipe 41.

Figure 13D:
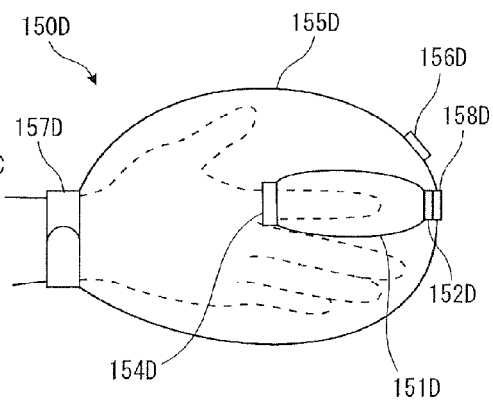

FIG. 13D is also a living body pressure bathing cover 150D for a hand part of the human body. This living body pressure bathing cover 150D is composed of an inner cover 151D covering the hand fingers, and an outer cover 155D covering the hand part and the inner cover 151D. The inner cover 151D has a supply port 152D connecting to the gas mist supply pipe 41 for introducing the gas mist and gas inside. The inner cover 151D is provided with a stopper 153D at its opening enabling to attach to and detach from the living body and avoiding leakage of the gas mist and gas sealed inside. The outer cover 155D is provided with a supply port 156D connecting to the gas mist supply pipe 41 for introducing the gas mist and gas inside. The outer cover 155B is provided with a stopper 157D and a connection part 158D, the stopper 157D enabling to attach to and detach from the living body and avoiding leakage of the gas mist and gas sealed inside, and the connection part 158D connecting the inner cover 151D to the gas mist supply pipe 41 while sealing the inside of the outer cover 155D by connecting the supply port 152B of the inner cover 151D and the gas mist supply pipe 41.

The living body pressure bathing covers 50, 150 mentioned in the first and second embodiments can be applied to various regions of the living body other than the examples illustrated up to now, and therefore, many other modifications are available. In particular, since the present invention can be practiced not only to the human bodies but also to whole of animals, shapes meeting to using objects and using regions are employed. In sum, if the shapes can cover the skin and mucous membrane of the living bodies and can form spaces for sealing the gas mist inside, any shapes can be employed.

Third Embodiment

Figure 14:
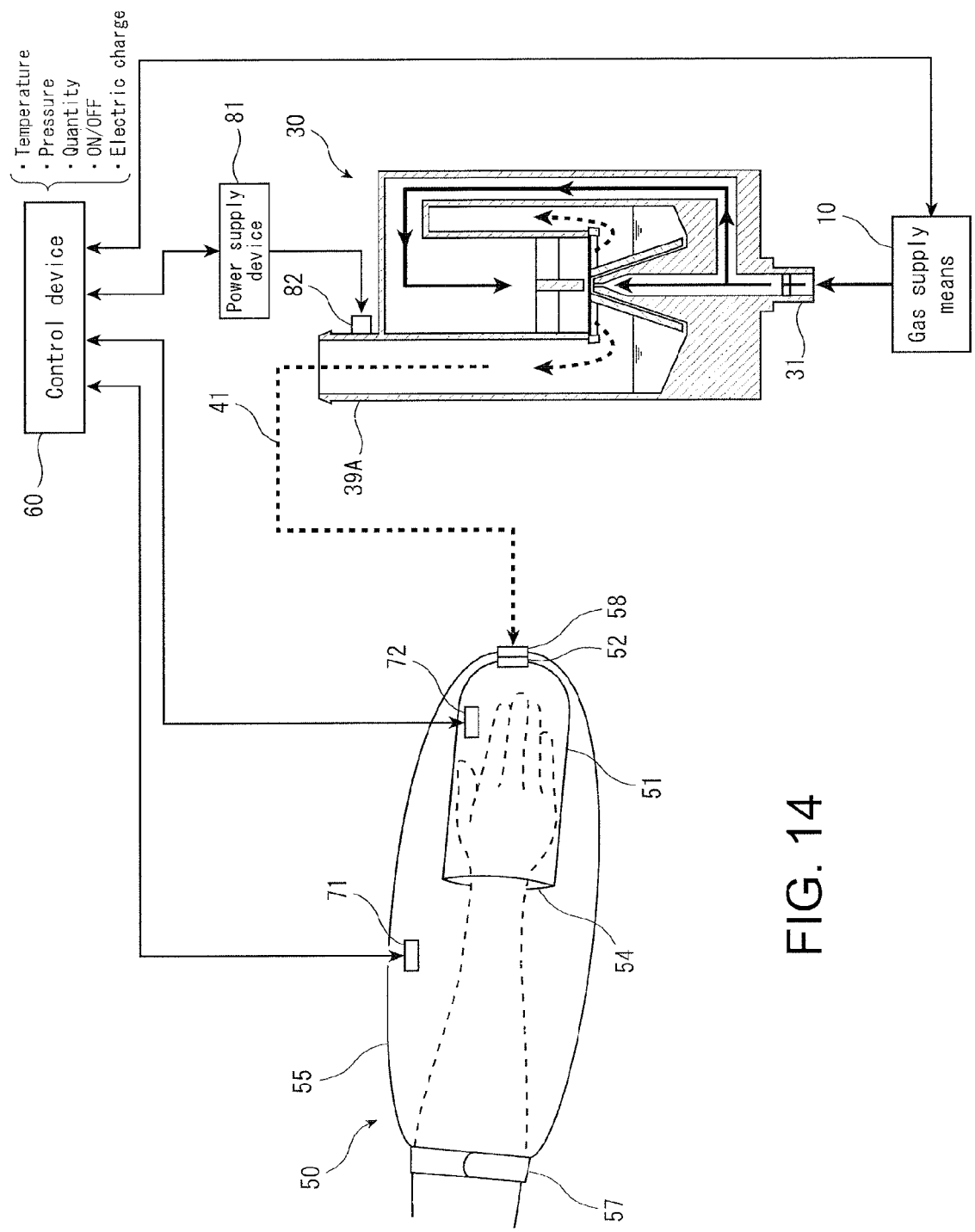

FIG. 14 is the whole schematic view of the gas mist pressure bathing system depending on the third embodiment of the present invention. This embodiment will explain the gas mist pressure bathing system having further an electric charge giving means for charging generated mist. As to the same parts as those of the first embodiment shown in FIG. 2, the same signs will be given to and detailed explanation will be omitted.

As showing in FIG. 14, the gas mist pressure bathing system disposes an electrode 82 in the vicinity of the gas mist discharge port 39A of the gas mist generator 30. The electrode 82 is connected to a power supply device 81, and sets a voltage value and controls ON/OFF by the control device 60.

The electrode 82 gives an electric charge (minus electric charge is desirous) when the gas mist and gas generated by the gas mist generator 30 are discharged. The mist is made thereby electrically charged and can heighten adherence to a charged material. That is, if heightening adherence to the skin and mucous membrane of the living body, an effect of improving absorption of gas by the gas mist pressure bathing is further heightened, and in case the above mentioned medicines are contained in the gas mist, it is made possible to more accelerate penetration into the skin and mucous membrane.

In the above mentioned respective embodiments, if a simple means like the cartridge system gas bomb is used for the gas supply means 10, it is possible to use the gas supply means 10 and the gas mist generator 30 (more preferably, the control device 60) under a compact condition of containing them in the case 20 as showing in FIG. 15. Herein, the gas supply means 10 has a regulator 10A. In FIGS. 16A to 16C, examples of using conditions are shown. As showing in FIGS. 16A to 16C, the cases 20 have stands 21, 22 or a hook 23 to stand upright, or the case 20 is suspended from a wall, so that the gas mist generator 30 is used as standing as possible. By such manners, the liquefied gas mist is easily recovered.

In the gas mist pressure bathing, the gas mist is contacted to the skin and mucous membrane of the living body at higher pressure than fixed by the living body pressure bathing covers 50, 150, and such pressurization is heightened in effect by pulse-shaped performance at predetermined intervals. Therefore, by supplying gas intermittently from the gas supply means 10 into the gas mist generator 30, the control device 60 may supply the gas mist into the living body pressure bathing covers 50, 150. Then, the effect is heightened by synchronizing rhythm of supplying to pulsation.

Having structured as above, according to the gas mist pressure bathing method and the gas mist pressure bathing system of the present invention, the gas mist pressure bathing effect can be improved by contacting the gas mist to the skin and mucous membrane of the living body sweated and easily absorbing the gas mist under the optimum pressurized condition.

The above references have explained the embodiments of the invention, but are not limited thereto, and so far as not deviating from the subject matter of the invention, various kinds of embodiments are, of course, available.

INDUSTRIAL APPLICABILITY

The invention relates to the gas mist pressure bathing method and the gas mist pressure bathing system for improving absorption efficiency of gas mist into the skin or the mucous membrane of the living body, in which the gas mist is prepared by pulverizing and dissolving oxygen or carbon dioxide, or mixed gas of oxygen and carbon dioxide and the liquid, and the gas mist is caused to directly contact the skin and mucous membrane of the living body at pressure of not less than the fixed value, and has industrial applicability.

EXPLANATION OF THE REFERENCE NUMERALS AND SIGNS

10: gas supply moans
10A: regulator
20: case
21, 22: stand
23: hook
30: gas mist generator
31: connection part
32: diverging part
33: liquid storage
34: nozzle
34A: front end open of the nozzle
35: liquid suction pipe-forming member
35A: liquid suction pipe
35B: front end part of the liquid suction pipe-forming member
36: baffle (collision member)
36A: baffle supporter
37: confluent part
38: gas introduction part
39: gas mist discharge part
39A: gas mist discharge port
41: gas mist supply pipe
41A: cornice shaped pipe
42: groove
50, 50A, 50B, 50C, 50D, 150, 150A, 150B, 150C, 150D: living body pressure bathing cover
51, 51A, 51B, 51C, 51D, 151, 151A, 151B, 151C, 151D: first cover (inner cover)
52, 52A, 52B, 52C, 52D, 152, 152A, 152B, 152C, 152D: supply port
153, 153A, 153B, 153C, 153D: stopper
54, 54A, 54B, 54C, 54D: opening
55, 5A, 55B, 55C, 55D, 155, 155A, 155B, 155C, 155D: second cover (outer cover)
156, 156A, 156B, 156C, 156D: supply port
57, 57A, 57B, 57C, 57D, 157, 157A, 157B, 157C, 157D: stopper
58, 58A, 58B, 58C, 58D, 158, 158A, 158B, 158C, 158D: connection part
60: control device
71, 71a, 71b: manometer
72: temperature gage
81: power supply device
82: electrode

The invention claimed is:

1. A gas mist pressure bathing method of causing carbon dioxide or oxygen, or a mixed gas (called as "gas" hereafter) of carbon dioxide and oxygen and a liquid which are pulverized and dissolved to turn out a mist (called as "gas mist" hereafter) at concentration of not less than a predetermined value to contact a skin or mucous membrane of a living body, comprising:
    (a) a first step of having an inside placed first cover and a second cover placed outside of the first cover to substantially seal the inside thereof, and supplying the gas mist and the gas mixed with the gas mist into a space of at least the first cover of a living body covering member for a predetermined time, the gas mist being supplied from the gas mist generation means,
    (b) a second step of discharging the gas mist and the gas from any one of the first cover and the second cover or from both, and
    (c) a third step of supplying the gas mist and the gas for the predetermined time into the first cover and the second cover from the gas mist generation means, and setting air pressure in at least the second cover to be within a predetermined range,
    wherein the first to third steps are repeated in multiple turns.

2. The gas mist pressure bathing method as set forth in claim 1, wherein a fourth step is provided after the third step for discharging the gas mist from the inside of the living body covering member.

3. The gas mist pressure bathing method as set forth in claim 1, wherein, in the first step and the third step, environments in the first cover or the second cover are controlled to be within ranges of predetermined values, based on one or plural sensors disposed within the first cover or second cover for measuring temperature, concentration of oxygen, concentration of carbon dioxide, or moisture.

4. The gas mist pressure bathing method as set forth in claim 1, wherein predetermined ranges of air pressure in the first cover and the second cover in the third step are 1.01 to 2.5 air pressure.

5. A gas mist pressure bathing system, which causes carbon dioxide or oxygen, or a mixed gas of carbon dioxide, oxygen (called as "gas" hereafter) and a liquid pulverized and dissolved to turn out a mist (called as "gas mist" hereafter) at concentration of not less than a predetermined value to contact a skin or mucous membrane of a living body, comprising:

a gas supply means of supplying the above mentioned gas, a gas mist generation means of generating the above mentioned gas mist with the gas supplied from the gas supply means and a liquid stored inside, and supplying the gas mist under a condition of mixing the gas, and a living body covering member which is a cover of covering the skin and mucous membrane of the living body and formed with a space for sealing inside the gas mist supplied from the gas mist generation means and the gas, furnishing a first cover placed inside and a second cover placed outside of the first cover and substantially sealing the inside of the first cover, wherein a covering region of the first cover is narrower than that of the second cover, and after contact of the gas mist to the covering region of the first cover, repeating contact of the gas mist to the covering region of the first cover and the covering region of the second cover, thereby to improve skin-pass absorption efficiency of the gas mist.

6. The gas mist pressure bathing system as set forth in claim 5, further provided with manometers of measuring pressure within the first cover and the second cover, and a control means of controlling air pressure within the first and the second covers to be within predetermined values on the basis of the measured values of the manometers.

7. The gas mist pressure bathing system as set forth in claim 5, further provided with one or plural sensors for measuring temperature, concentration of oxygen, concentration of carbon dioxide, or moisture within the first cover or the second cover, whereby the control means controls environments in the first cover or the second cover to be within predetermined values, based on the measured values of the sensor(s).

8. The gas mist pressure bathing system as set forth in claim 5, wherein the first cover has a shape of releasing the inside by the opening.

9. The gas mist pressure bathing system as set forth in claim 5, wherein the first cover has a shape of closing the inside.

10. The gas mist pressure bathing system as set forth in claim 5, wherein the first cover includes a hand palm or a foot sole in the covering region.

11. The gas mist pressure bathing system as set forth in claim 5, wherein the above mentioned liquid is any one or plural combination of water, ionic water, ozone water, physiological salt solution, purified water, or sterilized and purified water.

12. The gas mist pressure bathing system as set forth in claim 11, wherein the above mentioned liquid is any one or plural combination of menthol, vitamin E, vitamin C derivative, retinol, anesthetic agent, cyclodextrin, photo catalyst, complex of photo catalyst and apatite, hyaluronic acid, coenzyme Q10, seed oil, propolith, citric acid, ethanol, chlorhexidine gluconate, amphoteric surface active agent, benzalkonium chloride, alkyl diamino etherglycine acetate, sodium hypochlorite, peracetic acid, sodium sesquicarbonate, silica, povidone-iodine, sodium hydrogen carbonate, carbonate spring agent of high concentration, anti-allergic agent, anti-inflammatory agent, anti-febrile agent, anti-fungus agent, anti-influenza virus agent, influenza vaccine, steroid agent, anti-cancer agent, anti-hypertensive agent, cosmetic, or trichogen.

13. The gas mist pressure bathing system as set forth in claim 5, wherein, by the control means, gas is intermittently supplied from the gas supply means into the gas mist generation means to effect interval pressurization on the living body covering member.

14. The gas mist pressure bathing system as set forth in claim 5, wherein a size of the mist supplied from the gas mist generation means into the living body cover member is not larger than 10 µm.

15. The gas mist pressure bathing system as set forth in claim 5, wherein an electric charge giving means is provided for giving an electric charge to the mist supplied by the gas mist generating means.

16. The gas mist pressure bathing system as set forth in claim 15, wherein the electric charge is minus.

17. The gas mist pressure bathing system as set forth in claim 5, wherein the gas mist generation means has a gas mist supply pipe for supplying the gas mist and gas into the living body pressure bathing cover, and the gas mist supply pipe is furnished with a filter for removing liquid drops attaching to the inside of the pipe.

18. The gas mist pressure bathing system as set forth in claim 5, wherein the gas mist generating means has a gas mist supply pipe for supplying the gas mist and gas into the living body pressure bathing cover, and the gas mist supply pipe is composed of a cornice shaped pipe over a whole or at one part of the gas mist supply pipe.

19. The gas mist pressure bathing system as set forth in claim 18, wherein the cornice shaped pipe is formed inside with a groove in a shaft direction of the pipe.

20. The gas mist pressure bathing system as set forth in claim 5, wherein the gas mist generating means has a gas mist supply pipe for supplying the gas mist and gas into the living body pressure bathing cover, and the gas mist supply pipe is provided with a check valve.

21. The gas mist pressure bathing system as set forth in claim 5, wherein the first cover has a gas mist supply port for receiving supply of the gas mist and gas from the gas mist generation means, and the gas mist supply port is provided with a check valve.

22. The gas mist pressure bathing system as set forth in claim 5, wherein the second cover is provided with the gas mist supply port for supplying the gas mist and gas, and the gas mist supply port is provided with the check valve.

23. The gas mist pressure bathing system as set forth in claim 5, wherein the control means stops gas supply from the gas supply means when pressure value within the living body covering member exceeds a predetermined value.

* * * * *